United States Patent

Knapp et al.

[11] Patent Number: 5,984,965
[45] Date of Patent: Nov. 16, 1999

[54] ANTI-REFLUX REINFORCED STENT

[75] Inventors: Tracey E. Knapp, Coralville; John R. Frigstad; Michael J. Magliochetti, both of Iowa City, all of Iowa

[73] Assignee: UroSurge, Inc., Coralville, Iowa

[21] Appl. No.: 08/920,300

[22] Filed: Aug. 28, 1997

[51] Int. Cl.[6] ..................................................... A61F 2/04
[52] U.S. Cl. .............................. 623/12; 623/1; 606/127; 604/9
[58] Field of Search ..................... 623/1, 2, 12; 606/198, 606/127; 604/9

[56] References Cited

U.S. PATENT DOCUMENTS

| | | | |
|---|---|---|---|
| 4,434,797 | 3/1984 | Silander . | |
| 4,515,593 | 5/1985 | Norton | 604/265 |
| 5,019,102 | 5/1991 | Hoene | 623/12 |
| 5,069,899 | 12/1991 | Whitbourne et al. | 424/56 |
| 5,129,910 | 7/1992 | Phan et al. | 606/127 |
| 5,282,847 | 2/1994 | Trescony et al. | 623/1 |
| 5,380,270 | 1/1995 | Ahmadzadeh | 604/9 |
| 5,464,450 | 11/1995 | Buscemi et al. | 623/1 |
| 5,525,348 | 6/1996 | Whitbourne et al. | 424/423 |
| 5,542,928 | 8/1996 | Evans et al. | 604/113 |
| 5,556,426 | 9/1996 | Popadiuk et al. | 623/1 |
| 5,593,403 | 1/1997 | Buscemi | 606/2 |
| 5,647,843 | 7/1997 | Mesrobian et al. | 604/8 |
| 5,769,882 | 6/1998 | Fogarty et al. | 623/1 |

FOREIGN PATENT DOCUMENTS

| | | |
|---|---|---|
| 0808613 | 11/1997 | European Pat. Off. . |
| 9306792 | 4/1993 | WIPO . |
| 9307924 | 4/1993 | WIPO . |
| 9725090 | 7/1997 | WIPO . |

*Primary Examiner*—Paul B. Preblilic
*Attorney, Agent, or Firm*—Thomas J. Engellenner; Ronald E. Cahill; Nutter, McClennen & Fish, LLP

[57] ABSTRACT

A stent for maintaining the patency of a body passage including an elongate flexible body, at least one lumen extending the length of the body, a filament disposed along the elongate flexible body for inhibiting the fracture of the body within the body passage, and a valve for preventing the passage of fluid along the lumen in one direction. The filament is helically wound about the length of the elongate body. Hydrophilic and microbial coatings are applied to the surfaces of the stent and the stent is preferably constructed of a bioresorbable material.

15 Claims, 2 Drawing Sheets

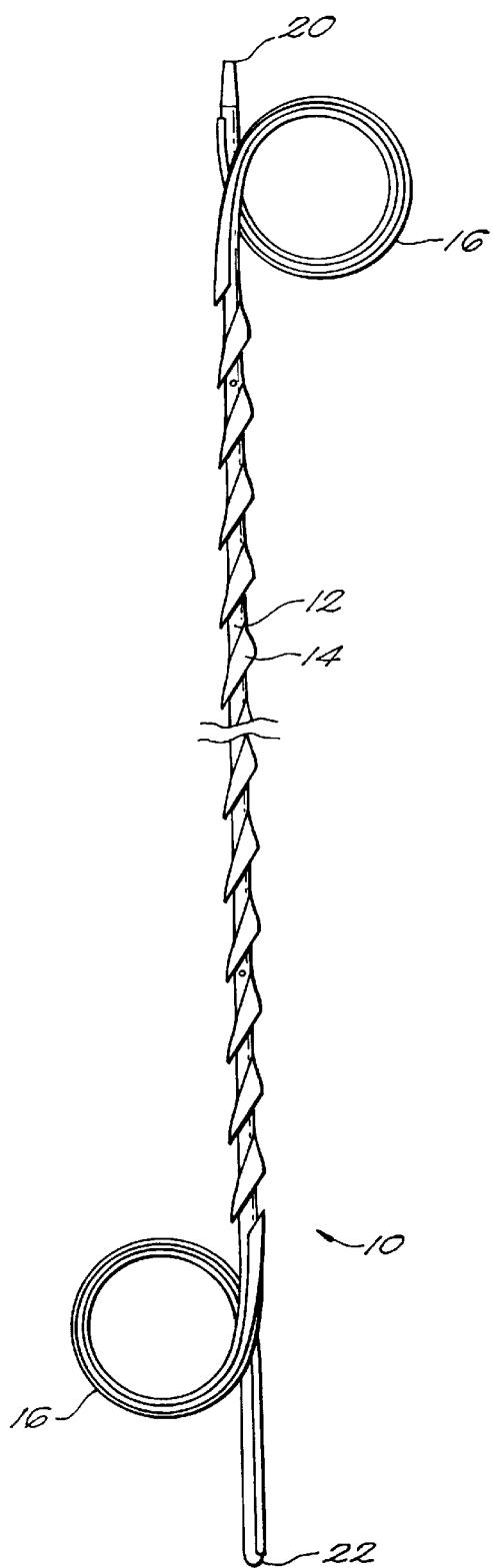
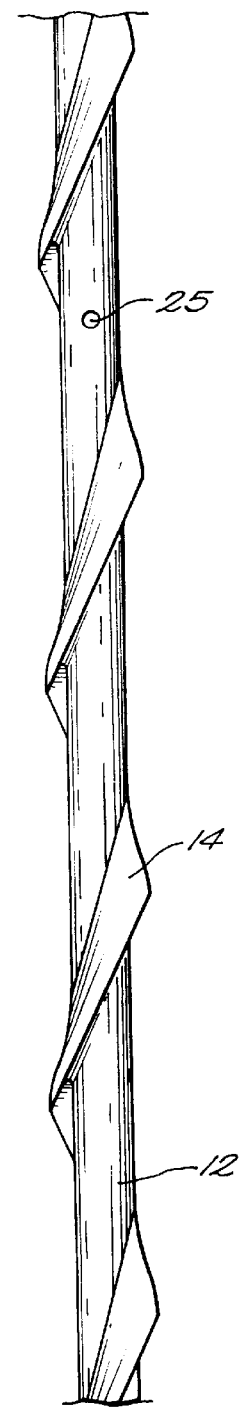
*FIG. 1*     *FIG. 2A*

ANTI-REFLUX REINFORCED STENT

FIELD OF THE INVENTION

The present invention relates generally to stents for maintaining the patency of body passages. More particularly, the invention relates to a stent for removing stones and their fragments from the luminal passages of the human body.

BACKGROUND OF THE INVENTION

Stents are commonly used for the treatment of body passages afflicted with hard irregular, masses, such as stones and stone fragments. Stones and stone fragments frequently develop within the urinary tract, including the kidneys, ureters, bladder, and the urethra, and can also develop in the other specific body passages, such as the biliary, salivary, and vascular passages. Conventional stents, such as the stent described in U.S. Pat. No. 5,129,910, for treatment of such masses comprise an elongate, flexible tubular body and generally include a central lumen extending the length of the body. Typically, the stent is provided with a series of spaced-apart barriers in the form of a ridge disposed along a portion of the stent body for urging the masses out of the body.

During treatment, the stent is inserted into the afflicted body passage and provides for passage of fluid through the lumen. The stones and stone fragments are urged out of the body passages either through the lumen or along the exterior surface of the stent. At the conclusion of the treatment, the stent is removed from the body passage.

Problems have developed with use of such stents due to the tendency of the stents to fracture within the body passage. Crystal encrustation of the stent during implantation results in a loss of elasticity leading to an increased likelihood of fracturing. Stent fracturing can occur during the treatment process or as the stent is removed from the body passage and is more likely during treatments requiring long term implantation of the stent. Fracturing can cause fragmenting of the stent into multiple pieces within the body passage and can result in stent fragments becoming lodged in the body passage. Removal of the stent fragments can be problematic, often requiring additional medical procedures and even surgery.

As such, there is a need for a stent for maintaining the patency of body passages that includes a reinforcing element for inhibiting the fracturing of the stent and aiding in removal of the stent.

Other problems are known with conventional stents. Specifically, reflux, particularly during treatment of the urinary tract, often occurs with such stents, resulting in the passage of fluid within the lumen of stent in a direction opposite the intended direction. During treatment of the urinary tract, the stent is inserted into the ureter between the kidney and the bladder and provides for fluid (urine) passage from the kidney to the bladder through the lumen of the stent. As bladder pressure increases, urine reflux occurs and urine begins to pass through the stent from the bladder back into the ureter, and potentially to the kidney.

As such, there is a need for a stent for maintaining the patency of a body passage that decreases reflux through the stent lumen.

It is an object of the invention to provide a reinforced stent for maintaining the patency of body passages that is less likely to fracture during treatment of the body passage.

It is another object of the invention to provide a stent for maintaining the patency of a body passage that decreases reflux through the stent.

It is a further object of the present invention to provide a stent that is inexpensive to manufacture and easy to use.

SUMMARY OF THE INVENTION

The present invention is directed to a stent for placement in a body passage and a method of making a stent. In accordance with a first embodiment of the invention, the stent includes an elongate flexible body and a reinforcing element, such as a filament, disposed along the elongate flexible body for inhibiting the fracture of the body within the body passage. The stent may include a barrier disposed along the elongate body for urging masses, such as stones and their fragments, out of the body passages by permitting passage of the masses in one direction along the stent. The stent may also include a self-retaining element for retaining the elongate body within the body passage.

In accordance with another aspect of the invention, the reinforcing element is a filament that is helically wound about the elongate flexible body.

In accordance with a further aspect of the invention, the filament extends along the entire length of the elongate body.

In accordance with still another aspect of the present invention, the filament is bonded to the outer surface of the elongate body.

In accordance with a further aspect of the invention, the elongate body, the barrier, and the self-retaining element each include a smooth, hydrophilic surface.

In accordance with a further aspect of the invention, the stent includes an anti-microbial treatment for inhibiting microbial deposition on the stent. The anti-microbial treatment can be an anti-microbial coating applied to the surface of the stent or, in the alternative, the stent material can include an anti-microbial treatment. Specifically, the stent material can be a polymer doped with an anti-microbial treatment such as silver ions.

In accordance with a further aspect of the invention, the stent is constructed of a bioresorbable material such as resorbable lactide polymer.

In accordance with a second embodiment of the invention, the stent includes an elongate flexible body, at least one lumen extending the length of the elongate body, and a device, such as a valve, for preventing the passage of fluid along the lumen in one direction. Preferably the valve is located at the distal end of the elongate body. The valve can be a slit valve, a ball valve, a duck-bill valve, or any other suitable valve.

In accordance with a third embodiment of the invention, the stent includes an elongate flexible body, at least one lumen extending the length of the body, a reinforcing element, such as a filament, disposed along the elongate flexible body for inhibiting the fracture of the body within the body passage, and a device, such as a valve, for preventing the passage of fluid along the lumen in one direction.

In a method of the present invention, a stent for maintaining the patency of a body passage is made. The method of the present invention includes the steps of providing a filament for reinforcing the elongate body of the stent and forming the elongate body by extrusion of a material, such as a polymer, and the filament through a die such that the filament is integrally formed within the stent.

In another aspect of the invention, the method includes the step of twisting the elongate body and the filament after the extrusion process such that the filament is helically wound about the elongate flexible body.

BRIEF DESCRIPTION OF THE DRAWINGS

These and other features and advantages of the present invention will be more fully understood by reference to the following detailed description in conjunction with the attached drawings in which like reference numerals refer to like elements and in which:

FIG. 1 is a side elevational view of the stent of the present invention.

FIG. 2A is an enlarged side elevational view of the elongate flexible body of the stent of the present invention.

DETAILED DESCRIPTION

Figure 2B:
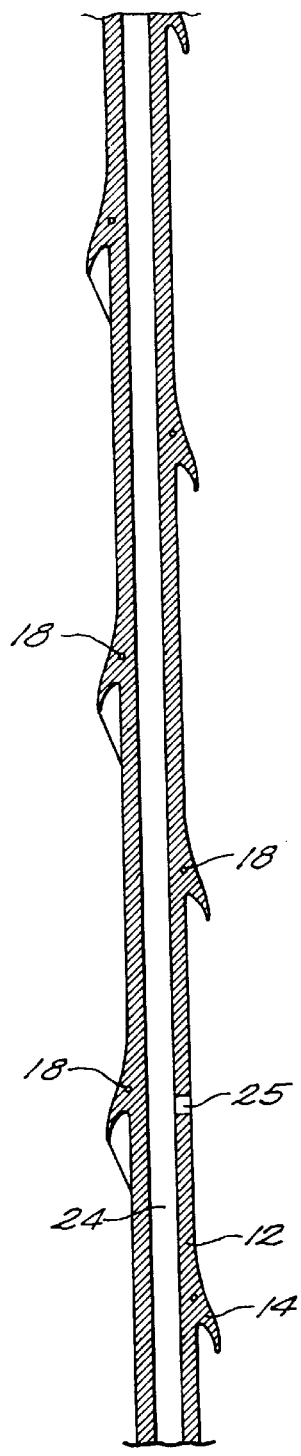
FIG. 2B is an enlarged cross-sectional view of the elongate flexible body of the stent of the present invention, showing the lumen and the filament.

A stent 10 for placement in a body passage and maintaining the patency of the body passage is shown in FIG. 1. The components of the stent include an elongate flexible body 12, a ridge 14 defining a series of spaced apart barriers for transporting masses and fluid along the body 12, and two self-retaining elements 16 for retaining the stent 10 in the body passage. The structure and operation of each of these components is described in detail in U.S. Pat. No. 5,129,910, which is incorporated herein by reference.

The elongate, flexible body 12 includes a proximal end 20 and a distal end 22. The stent can include a single central lumen 24 or a plurality of parallel lumens extending from the proximal end 20 to the distal end 22 and providing a passage for fluid and masses through the body 12. In the alternative, the stent can be constructed without the lumen such that the body 12 is a solid tube and fluid and masses are permitted only to travel along the ridge 14, on the exterior surface the body 12. The solid design of the body 10 provides increased strength for the stent 10, thus decreasing the possibility of fracturing of the stent 10 in the body passage, but limits the rate of fluid removal by the stent. The solid design also decrease the likelihood of reflux.

One of the self-retaining elements 16 is disposed at the distal end 20 and the other at the proximal end 22. The self-retaining element 16 can be in the form of "J" or a "pig tail" as shown in FIG. 1, or in any other shape suitable for preventing migration of the stent relative to the body passage.

To permit fluid communication between the central lumen 24 and a region exterior to the stent 10, the body 12 of the stent includes a plurality of passageways 25 in the form of oval holes. Those skilled in the art will appreciate a variety of other configurations and structures which may function as the radial passageways 25. The passageways may include, for example, fenestrations, vents, membranes, screens, pores, and the like. Preferably, passageways 25 are sufficiently large to prevent occlusion with mucus, cellular or proteinaceous debris, particulate matter, and the like. In addition, passageways 25 may be sufficiently large to accommodate smaller masses, such as stone fragments, which may pass to the central lumen 24 for rapid removal from the body passage.

In some applications, it may be advantageous to construct the stent of a bioresorbable material, such as resorbable lactide polymer (poly-L-lactic acid), such that the removal of the stent from the body passage is unnecessary. One skilled in the art will appreciate that the degree of resorbtion can be controlled through the selection of the bioresorbable material to be used. Such control permits the stent to be configured for both short and long term implantation. Bioresorbable stents and methods for accelerating their decomposition are described in U.S. Pat. No. 5,593,403, incorporated herein by reference.

The stent components, including the body 12, the ridge 14, and the self-retaining elements 16, can include a smooth, hydrophilic surface to ensure a smooth transition of the stent over the tissue of the body passage. The hydrophilic surface can be prepared by forming the components with a hydrophilic polymer, by grafting a hydrophilic polymer layer, or, preferably, by applying a hydrophilic coating to the stent components. The hydrophilic surface can reduce the degree of tissue reaction, particularly from the self-retaining elements 16, at the site in the body passage at which the stent is positioned. Suitable hydrophilic coatings can include polyvinylpyrrolidone and cellulose esters formulated in an organic solvent, such as, for example, SLIP-COAT™, sold by STS Biopolymers of Henrietta, N.Y.

Preferably, the stent includes an anti-microbial treatment in the form of a coating applied to the surfaces of the stent or as a component of the material forming the stent. The anti-microbial treatment can also be added to a hydrophilic coating that is applied to the surface of the stent components. The anti-microbial treatment acts to minimize the degree of microbial deposition on the surface of the stent, thereby decreasing the potential of infection. Such anti-microbial treatments include, for example, silver ions doped in a polymer stent material. Examples of other suitable anti-microbial treatments are described in U.S. Pat. Nos. 5,525,348 and 5,069,899, incorporated herein by reference.

Referring to FIGS. 1 and 2B, the first embodiment of the present invention will be described. A filament 18, such as a suture filament, preferably having a high tensile strength, is wound about the exterior surface of the body 12 of the stent. The filament reinforces the body along its longitudinal axis and inhibits fracturing of the body, especially when the stent is removed from the body passage. Preferably, the filament 18 extends the entire length of the body, including along the self-retaining means 16. In the alternative, the filament 18 can be disposed about a segment or a plurality of segments of the body 12 to selectively reinforce portions of the stent.

In the preferred embodiment, the filament 18 is formed within the ridge 14 such that the filament is helically wound about the body 12, as shown in FIG. 2B. The filament can be positioned during the process of making the stent by extrusion of the stent material, such as a polymer, together with the filament through a die such that the filament is formed within the bulked portion of the ridge 14. As the extruded material, including the filament, emerges from the die, the material is twisted such that the filament is helically wound about the body 12 of the stent.

In alternative embodiments, the filament can be bonded to the exterior surface of the body 12, an interior surface of the body 12 if the stent includes a lumen, or the exterior surface of the ridge 14. In addition, the filament 18 need not be wound about the body 12 but can be disposed linearly or coiled along the body 12. One skilled in the art will appreciate that is preferable to provide the filament in a location other than on the exterior surface of the stent so that the filament does not interrupt the smooth surface of the stent and thus, potentially interfere with the insertion or removal of the stent.

The filament 18 is useful for inhibiting fracturing of the stent 10, particularly when the stent is removed from the patient's body. Frequently when conventional stents, such as the stent described in U.S. Pat. No. 5,129,910, are removed from the patient's body the stent cracks or can separate into multiple pieces. Such fracturing is more likely to occur after long term implantation of the stent. If such fracturing occurs, the separated pieces can potentially become lodged in the patient's body. The presence of the filament reinforces the stent and inhibits fracturing by increasing the tensile strength of the stent along its longitudinal axis. In addition, if fracturing does occur, the filament aids in the removal of the entire stent by holding the fractured segments together during the removal.

The increase in tensile strength provided by the filament permits the stent to be constructed using less material thereby reducing manufacturing costs. Importantly, if the body 12 of the stent includes a central lumen or a plurality of lumens, the diameter of the lumen or lumens can be increased by reducing the wall thickness of the stent, without a resulting weakening of the stent. The increased diameter of the lumen provides for an increased flow rate through the stent and allows for the passage of larger stones and stone fragments through the stent.

Figure 3A:
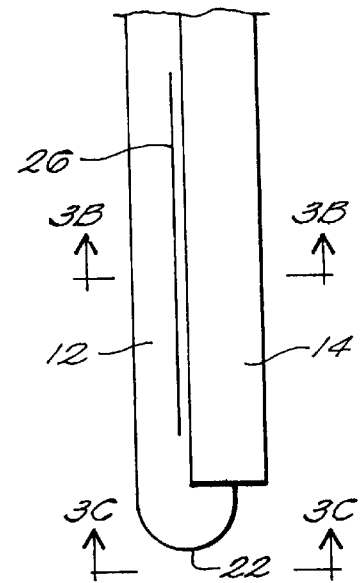
FIG. 3A is a side elevational view of the distal end of the elongate flexible body of the stent of the present invention.
Figure 3B:
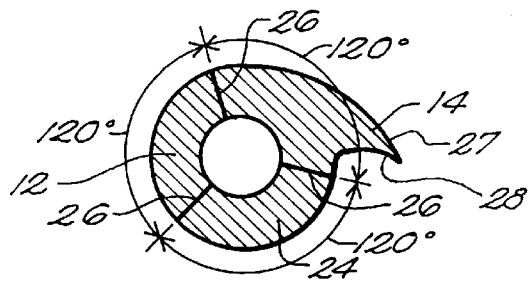
FIG. 3B is a cross-sectional view of the elongate flexible body taken along the line B—B.
Figure 3C:
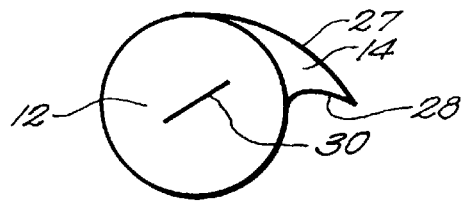
FIG. 3C a rear elevational view of the elongate flexible body of the stent of the present invention, showing the distal end of the stent and the slit valve.

Referring to FIGS. 3A–C, a second embodiment of the present invention will be described. FIG. 3A shows the distal end 22 of the elongate flexible body 12 and the ridge 14 of the stent 10. As shown in FIG. 3B, the stent 10 includes a central lumen 24 formed in the body 12 and extending to the distal end 22. The distal end 22 of the body 12 includes a slit valve defined by a plurality of longitudinal slits 26 formed in the wall of the body 12. In the open position, the slits 26 permit fluid passage from the central lumen 24 of the stent.

The slits 26 forming the slit valve are normally closed and permit fluid passage into the central lumen 24 only in the direction from the proximal end 20 to the distal end 22, indicated by arrow A. Thus, an increase in fluid pressure within the central lumen 24 results in the slits opening and allows fluid passage out of the stent. Conversely, an increase in external fluid pressure at the distal end 22 of the stent will force the slits 26 closed and prohibit fluid flow into the central lumen, i.e. in the direction indicated by arrow B. Thus, reflux of fluid through the lumen of the stent is prevented.

A stent having the described slit valve is particularly useful for the treatment of stone and stone fragments within the urinary tract between the kidney and the bladder. The stent 10 is inserted into the urinary tract such that the proximal end 24 faces the kidney and the distal end 24 faces the bladder. The central lumen 26 is open at the proximal end 20 such that fluid (urine) from the kidney is free to enter the central lumen. The slits 26 defining the slit valve open with an increase of urine pressure in the central lumen and urine is permitted to empty into the bladder.

When fluid pressure in the bladder begins to increase, the slits 26 defining the slit valve close and prevent passive urine reflux back into the urinary track (Arrow B) and, potentially into the kidney.

The number and length of slits 26 used to from the slit valve can vary depending on the procedure for which the stent is used. Increasing the quantity or length of the slits increases the flow rate of fluid exiting the lumen of the stent through the slit valves. Likewise, the material of the stent body, in addition to the number and length of the slits defining the slit valve, can be adjusted to select the desired lumen fluid pressure at which the slits will open.

It is preferable to form the slit valve using three longitudinal slits positioned 120 degrees apart on the stent body 12. However, it is not necessary for the slits to be aligned along the longitudinal axis of the stent body 12 as shown in FIG. 3A. Alternate orientations, including slits positioned transverse to the longitudinal axis of the stent body, can be used.

One skilled in the art will appreciate that other valves may be used in place of the slit valve, such as duck-bill valves and ball valves.

As shown in FIG. 3C, the central lumen 24 terminates at a terminal slit 30 formed in the distal end 22 of the stent body. The terminal slit 30 is provided to permit the stent to pass along a guide wire during insertion of the stent into a body passage. Prior to insertion of the stent into the body passage, the guide wire (not shown), having a diameter less than that of the central lumen of the stent, is inserted into the body passage. The stent is positioned about the guide wire such that the guide wire is located in the central lumen of the stent and extends through the terminal slit 30. The stent is inserted into the body passage by sliding it along the guide wire into the body passage. The guide wire is then removed through the terminal slit 30.

It is to be understood that the present invention is not limited to the embodiments described above, but encompasses any and all embodiments within the scope of the following claims:

What is claimed is:

1. A stent for placement in a body passage, said stent comprising:

an elongate flexible body having a proximal and a distal end, means disposed along said elongate body for defining a series of spaced-apart barriers which, when said stent is placed in said body passage, permit the passage of masses from said proximal end to said distal end but not in the opposite direction, means on said elongate flexible body for self-retaining said body in place within said body passage, and a high tensile strength filament disposed within the means for defining spaced-apart barriers and extending along said elongate body for increasing the tensile strength of said elongate flexible body such that fracturing of said elongate flexible body is inhibited.

2. The stent according to claim 1, wherein said filament is helically wound about said elongate flexible body.

3. The stent according to claim 1, wherein said filament extends from said proximal end to said distal end of said elongate body.

4. The stent according to claim 1, wherein said filament is bonded to an outer surface of said elongate flexible body.

5. The stent according to claim 1, wherein said filament is disposed about a particular section of said elongate body to selectively reinforce said particular section.

6. The stent according to claim 1, wherein each of said elongate flexible body, said means for defining a series of spaced-apart barriers, and said means for self-retaining said body include a smooth, hydrophilic surface.

7. The stent according to claim 1, wherein said stent includes an anti-microbial coating disposed on a surface of said stent for inhibiting microbial deposition on said surface.

8. The stent according to claim 1, wherein said stent is constructed from a material having an anti-microbial treatment formed therein.

9. The stent according to claim 8, wherein said material comprises a polymer and said anti-microbial treatment comprises silver ions doped in said polymer.

10. The stent according to claim 1, wherein said stent is constructed of a bioresorbable material.

11. The stent according to claim 10, wherein said bioresorbable material is a resorbable lactide polymer.

12. The stent according to claim 1, wherein said elongate body is of solid construction.

13. A stent for placement in a body passage, said stent comprising:

an elongate flexible body having a proximal and a distal end and at least one lumen extending from said proximal to said distal end, means disposed along said elongate flexible body for defining a series of spaced-apart barriers which, when said stent is placed in said body passage, permit the passage of masses from said proximal end to said distal end but not in the opposite direction, means on said elongate flexible body for self-retaining said body in place within said body passage, a slit valve disposed at said distal end of said elongate body for preventing the passage of fluid along said lumen from said distal end to said proximal end, and a high tensile strength filament disposed within the means for defining spaced-apart barriers and extending along said elongate body for increasing the tensile strength of said elongate flexible body such that fracturing of said elongate flexible body is inhibited.

14. The stent according to claim 13, wherein each of said elongate flexible body, said means for defining a series of spaced-apart barriers, and said means for self-retaining said body include a smooth, hydrophilic surface.

15. The stent according to claim 13, wherein said stent includes an anti-microbial coating disposed on a surface thereof for inhibiting microbial deposition on said surface.

* * * * *